United States Patent
Kitazono et al.

(10) Patent No.: US 8,263,187 B2
(45) Date of Patent: Sep. 11, 2012

(54) COMPOSITE OF SUPPORT MATRIX AND COLLAGEN, AND METHOD FOR PRODUCTION OF SUPPORT MATRIX AND COMPOSITE

(75) Inventors: Eiichi Kitazono, Tokyo (JP); Takanori Miyoshi, Tokyo (JP); Hiroaki Kaneko, Tokyo (JP); Yoshihiko Sumi, Tokyo (JP); Yukako Fukuhira, Tokyo (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 13/031,934

(22) Filed: Feb. 22, 2011

(65) Prior Publication Data

US 2011/0140312 A1    Jun. 16, 2011

Related U.S. Application Data

(62) Division of application No. 10/551,192, filed as application No. PCT/JP2004/004620 on Mar. 31, 2004, now abandoned.

(30) Foreign Application Priority Data

Mar. 31, 2003  (JP) ................................. 2003-094399
Nov. 13, 2003  (JP) ................................. 2003-383432

(51) Int. Cl.
  *B05D 1/04*  (2006.01)
  *B05D 1/22*  (2006.01)
  *A61F 2/00*  (2006.01)
(52) U.S. Cl. .................... 427/458; 424/426; 427/459
(58) Field of Classification Search .................. None
  See application file for complete search history.

(56) References Cited

U.S. PATENT DOCUMENTS

| 3,463,158 A | 8/1969 | Schmit et al. |
| 4,870,966 A | 10/1989 | Dellon et al. |
| 5,298,276 A | 3/1994 | Jayaraman |
| 5,697,970 A * | 12/1997 | Schmitt et al. ............... 623/1.51 |
| 6,090,117 A | 7/2000 | Shimizu |
| 6,576,019 B1 | 6/2003 | Atala |
| 2002/0090725 A1 * | 7/2002 | Simpson et al. ............. 435/402 |

FOREIGN PATENT DOCUMENTS

| EP | 0 956 833 A2 | 11/1999 |
| GB | 1 265 246 | 3/1972 |
| GB | 1 577 221 | 10/1980 |
| JP | 52-110977 A | 9/1977 |

(Continued)

OTHER PUBLICATIONS

Japanese Industrial Standard for Surface Roughness (JIS B 0601-2001); 3 pages; published 2001; downloaded Apr. 23, 2012.*

(Continued)

*Primary Examiner* — Robert A Wax
*Assistant Examiner* — Jeffrey T Palenik
(74) *Attorney, Agent, or Firm* — Sughrue Mion, PLLC

(57) ABSTRACT

A cylindrical body is produced which is composed of a fiber structure with a basis weight of 1-50 g/m$^2$ and having a diameter of 0.5-50 mm and a bellows-shaped section, wherein the crest-to-crest spacing of the bellows-shaped section is no greater than 2 mm and the crest-to-valley depth of the bellows-shaped section is 0.01-1 mm; collagen is added to the cylindrical body to produce a composite including the cylindrical body and collagen.

3 Claims, 1 Drawing Sheet

FOREIGN PATENT DOCUMENTS

| | | |
|---|---|---|
| JP | 61-045766 A | 3/1986 |
| JP | 62-186864 A | 8/1987 |
| JP | 5-23362 A | 2/1993 |
| JP | 5-337143 A | 12/1993 |
| JP | 6-285150 A | 10/1994 |
| JP | 7-148243 A | 6/1995 |
| JP | 8-33661 A | 2/1996 |
| JP | 08-056968 A | 3/1996 |
| JP | 8-71093 A | 3/1996 |
| JP | 8-294530 A | 11/1996 |
| JP | 9-173361 A | 7/1997 |
| JP | 10-244009 A | 9/1998 |
| JP | 2001-521789 A | 11/2001 |
| JP | 2002-159502 A | 6/2002 |
| JP | 2003-126125 A | 5/2003 |
| WO | 98/22155 A1 | 5/1998 |
| WO | 98/24385 A1 | 6/1998 |

OTHER PUBLICATIONS

International Preliminary Report on Patentability (Translation); PCT/JP2004/004620; International Filing Date Mar. 31, 2004; Priority Date, Mar. 31, 2003.

Japanese Office Action, corresponding to JP Appln. No. 2005-504267, dated Jan. 26, 2010.

English language translation for JP-A-61-045766; Publication date: Mar. 5, 1986; Applicant: Toshiki Hiroyoshi.

http://www.onlineconversion.com/length_all.htm (website for unit conversion), dated Aug. 24, 2009.

* cited by examiner

COMPOSITE OF SUPPORT MATRIX AND COLLAGEN, AND METHOD FOR PRODUCTION OF SUPPORT MATRIX AND COMPOSITE

CROSS REFERENCE TO RELATED APPLICATIONS

This is a divisional of U.S. application Ser. No. 10/551,192 filed Sep. 29, 2005, which is a 371 of PCT/JP2004/004620 filed Mar. 31, 2004, the disclosures of all of which are hereby incorporated by reference.

TECHNICAL FIELD

The present invention relates to a composite composed of collagen and a cylindrical support matrix with a bellows-shaped section made of a fiber structure composed of aliphatic polyester fibers with a mean fiber size of 0.05-50 μm, to a cylindrical support matrix having a bellows-shaped section, and to a method for production of the support matrix and a method for production of the composite.

BACKGROUND ART

Recent years have seen an increase in active research in regenerative medicine, a technical field which takes advantage of the ability of cells to differentiate and proliferate to achieve reconstruction of original biological tissues and organs, as a method for treating major injury to or loss of biological tissue and organs. Neural regeneration is a branch of this field, and research is underway toward using tubes composed of artificial materials for crosslinking between stumps in the neuron-deficient sites of patients with ablated neural tissue, to induce regeneration of the neural tissue. Such tubes are made of silicon, polyurethane, polylactic acid, polyglycolic acid, polycaprolactone or their copolymers or composites, and they are often internally coated with collagen or laminin.

For vascular regeneration there are used artificial material tubes made of polytetrafluoroethylene, polyester, polylactic acid, polyglycolic acid, polycaprolactone or their copolymers or composites, and these are also often internally coated with gelatin, albumin, collagen or laminin.

For example, Japanese Unexamined Patent Publication HEI No. 6-285150 describes artificial vessels obtained by injecting insoluble collagen into the walls of cylindrical tubes made of a fibrous substance, and then subjecting them to chemical treatment before drying.

Also, Japanese Unexamined Patent Publication HEI No. 7-148243 discloses an implant material whose matrix is a biocompatible bulky structure comprising organic fibers in a three-dimensional woven texture or knitted texture, or a composite texture obtained as a combination thereof, wherein the void fraction of the texture is preferably 20-90 vol %.

Japanese Unexamined Patent Publication HEI No. 8-294530 describes a cardiovascular restorative material characterized by insolubilizing a bioabsorbable substance attached to a porous matrix by at least one means having a physical effect of wet swelling by entanglement, heat treatment and charging.

Japanese Unexamined Patent Publication HEI No. 8-33661 describes an artificial vessel obtained by coacervation of water-soluble elastin and fixing with a crosslinking agent, either directly or after coating of gelatin or collagen and fixing with a crosslinking agent, onto the lumen surface of an artificial vessel matrix made of a synthetic resin.

Also, Japanese Unexamined Patent Publication HEI No. 9-173361 describes an artificial vessel obtained by coating of albumin onto the lumen surface of an artificial vessel matrix made of a synthetic resin, and heating thereof or further crosslinking thereof with a crosslinking agent after the heating to construct an albumin layer, followed by coacervation of water-soluble elastin thereover and fixing with a crosslinking agent.

Japanese Unexamined Patent Publication No. 2003-126125 describes an artificial vessel having a cylindrical porous artificial vessel matrix, wherein the pores of the porous artificial vessel matrix are impregnated with a gel solution containing a biofunctional substance.

These publications describe tubes having synthetic resins woven into a plain weave or knit as the matrix for an artificial vessel, nonwoven fabric tubes formed from a synthetic resin shaped into a filament and roll laminated on a mandrel, or tubes obtained by extrusion molding of a mixture of a synthetic resin and a particulate aqueous solution of sodium chloride, but all of these methods yield artificial vessel matrix tubes which lack stretchability and have unsatisfactory Young's moduli.

A modification for improving stretchability by means of a special shape is described in Japanese Unexamined Patent Publication HEI No. 5-23362, which discloses an artificial tube obtained by using multifilament yarn composed of polyester ultrafine filaments as the warp and weft yarns, and hollow weaving to yield a seamless tube which is then worked to form a bellows-shaped section.

Also, Japanese Unexamined Patent Publication HEI No. 8-71093 discloses a modification whereby pleats are added to a conical fabric prosthetic vessel whose starting material is a fiber material.

Since the aforementioned silicon, polyurethane, polytetrafluoroethylene and polyester materials lack bioabsorption properties, they are associated with problems from the standpoint of long-term safety, while compression and damage to regenerated nerves and vessels is also a concern. Also, polylactic acid, polyglycolic acid, polycaprolactone and their copolymers, while having bioabsorption properties, are problematic in terms of Young's modulus and stretchability, and can likewise lead to compression and damage to regenerated nerves and vessels. In other words, no tubes are known at the current time which exhibit superior performance from the standpoint of bioabsorption, Young's modulus and stretchability.

These problems can potentially be overcome by using composites of elastic materials such as collagen with support matrices made of polylactic acid, polyglycolic acid, polycaprolactone and their copolymers, but since conventionally known support matrices made of polylactic acid, polyglycolic acid, polycaprolactone and their copolymers lack stretchability, they counter the elastic property of the collagen and thus limit the use of such materials in the body. In other words, the currently known support matrices made of polylactic acid, polyglycolic acid, polycaprolactone and their copolymers, and composites of such support matrices with collagen, do not exhibit excellent stretchability.

DISCLOSURE OF THE INVENTION

It is an object of the present invention to provide a matrix having high stretchability and an adequate Young's modulus (elastic modulus), as a tube which can serve as the matrix for an artificial vessel or for neural regeneration.

More specifically, the object is to provide such a matrix wherein the tube is a polymer compound having a bioabsorption property.

The aspects of the present invention are as follows.

1. A composite comprising collagen and a support matrix made of a fiber structure composed of aliphatic polyester fibers with a mean fiber size of 0.05-50 μm.

2. A composite according to aspect 1 of the invention, wherein the fiber structure is a biodegradable polymer.

3. A composite according to aspect 2 of the invention, wherein the fiber structure is an aliphatic polyester.

4. A composite according to aspect 3 of the invention, wherein the aliphatic polyester is polylactic acid, polyglycolic acid, polycaprolactone or a copolymer thereof.

5. A composite according to aspect 1 of the invention, wherein the support matrix is a cylindrical body with a bellows-shaped section.

6. A composite according to aspect 5 of the invention, wherein the cylindrical body is a cylindrical body which is composed of a fiber structure with a basis weight of 1-50 g/m$^2$ and has a membrane thickness of 0.05-0.2 mm and a diameter of 0.5-50 mm, wherein the spacing of the bellows-shaped section is no greater than 2 mm and the depth of the bellows-shaped section is 0.1-10 mm.

7. A cylindrical body characterized by being composed of a fiber structure with a basis weight of 1-50 g/m$^2$ and having a membrane thickness of 0.05-0.2 mm and a diameter of 0.5-50 mm, wherein the spacing of the bellows-shaped section is no greater than 2 mm and the depth of the bellows-shaped section is 0.1-10 mm.

8. A cylindrical body according to aspect 7 of the invention, wherein the cylindrical body is a biodegradable polymer.

9. A composite according to aspect 8 of the invention, wherein the fiber structure is an aliphatic polyester.

10. A cylindrical body according to aspect 9 of the invention, wherein the aliphatic polyester is polylactic acid, polyglycolic acid, polycaprolactone or a copolymer thereof.

11. A cylindrical body according to aspect 7 of the invention, wherein the mean fiber size of the cylindrical body is 0.05-50 μm.

12. A method for production of a cylindrical body composed of a fiber structure with a basis weight of 1-50 g/m$^2$, wherein the spacing of the bellows-shaped section is no greater than 2 mm and the depth of the bellows-shaped section is 0.01-0.1 mm, which method comprises a stage of producing a solution of an aliphatic polyester in a volatile solvent, a stage of spinning the solution by an electrostatic spinning method, a stage of obtaining a fiber structure accumulated on a collector, and a stage of molding the fiber structure into a cylindrical body having a bellows-shaped section with a spacing of no greater than 2 mm.

13. A method for production of a composite composed of a cylindrical body and collagen, wherein a composite is formed of a cylindrical body produced by a method according to aspect 12 of the invention, and collagen.

14. A method for production of a composite composed of a cylindrical body and collagen, wherein a cylindrical body produced by a method according to aspect 12 of the invention is impregnated with a solution comprising collagen dissolved and/or dispersed in a solvent, and then at least one method is employed to fix the collagen by gelling, crosslinking or drying.

BEST MODE FOR CARRYING OUT THE INVENTION

Figure 1:
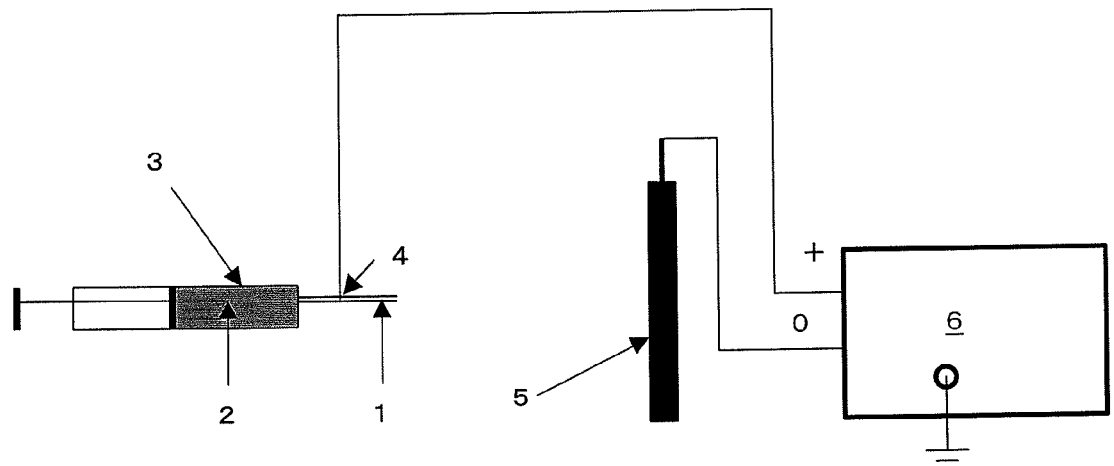
FIG. 1 is an example of an apparatus used in an electrostatic spinning method wherein the spinning solution is discharged into an electrostatic field, as a production method of the invention.

The present invention will now be explained in greater detail. The examples and explanation which follows are only illustrative of the invention and, needless to mention, modifications may be implemented which are within the scope of the invention.

The fiber structure used for the invention may be a three-dimensional structure formed by laminating and accumulating single or multiple filaments. The form of the structure may be, for example, a nonwoven fabric, woven fabric, knitted fabric, mesh, yarn or the like.

The composite used for the invention is a composite composed of the aforementioned fiber structure and collagen.

The fiber structure used for the invention is made of an aliphatic polyester.

As aliphatic polyesters there may be mentioned polylactic acid, polyglycolic acid, lactic acid-glycolic acid copolymer, polycaprolactone, polybutylene succinate, polyethylene succinate and their copolymers. Preferred aliphatic polyesters among these are polylactic acid, polyglycolic acid, lactic acid-glycolic acid copolymer and polycaprolactone, with polylactic acid and polycaprolactone being particularly preferred.

The fiber structure used for the invention is preferably a cylindrical body with a bellows-shaped section.

The fiber structure of the invention has a basis weight of 1-50 g/m$^2$, and is preferably not less than 1 g/m$^2$ because a structure will not be satisfactorily formed. It is also preferably not greater than 50 g/m$^2$ because the stretchability will be impaired when it is molded into a tube. A more preferred basis weight range is 5-30 g/m$^2$, and a particularly preferred basis weight range is 5-20 g/m$^2$.

The membrane thickness of the fiber structure is preferably 0.05-0.2 mm, and more preferably 0.1-0.18 mm.

The fiber structure of the invention is a cylindrical body with a diameter of 0.5-50 mm, wherein the spacing of the bellows-shaped section is no greater than 2 mm and the depth of the bellows-shaped section is 0.1-10 mm, because if the spacing is greater than 2 mm, the stretchability will be impaired when it is molded into a tube. The spacing of the bellows-shaped section is more preferably no greater than 1 mm.

The fiber structure of the invention is formed from fibers with a mean fiber size of 0.05-50 μm. The mean fiber size is preferably not less than 0.05 μm because the strength of the fiber structure will not be maintained. The mean fiber size is also preferably not greater than 50 μm because the stretchability may be reduced during molding into a tube, thus impairing the elastic modulus. A more preferred range for the mean fiber size is 0.2-25 μm, and a particularly preferred range for the mean fiber size is 0.2-20 μm. The range is most preferably 0.3-10 μm. The fiber size is the diameter of a fiber cross-section.

The mechanical properties of the fiber structure of the invention are preferably such that the Young's modulus is $1\times10^2$-$1\times10^7$ Pa and the yield elongation is 20% or greater. A Young's modulus of less than $1\times10^2$ or greater than $2\times10^7$, or a yield elongation of less than 20%, can lead to problems in terms of elasticity and stretchability, as well as compression and damage to regenerated neurons or vessels.

The method of producing the fiber structure of the invention may be an electrostatic spinning method, a spunbond method, a melt blow method, a flash spinning method or the like. Electrostatic spinning is preferred among these methods. In an electrostatic spinning method, a solution of the aliphatic polyester in a volatile solvent is discharged into an electrostatic field formed between electrodes, and the solution is drawn toward the electrodes and the formed fiber substance is collected. "Fibrous substance" includes not only one having the solvent of the solution already distilled off to form a fiber structure state, but also a substance still containing the solution solvent. The electrodes used for the invention may be composed of any type of substance which exhibits conductivity, such as metal or an inorganic or organic substance. They may also each consist of an insulator coated with a thin film of a conductive metal, inorganic or organic substance. The electrostatic field of the invention is formed between a pair of or more electrodes, and a high voltage may be applied to any of the electrodes. This includes, for example, cases using a total of three electrodes, i.e. two high-voltage electrodes with different voltage levels (for example, 15 kV and 10 kV) and an electrode which is grounded, as well as cases using more than three electrodes.

The concentration of the aliphatic polyester in the aliphatic polyester solution according to the invention is preferably 1-30 wt %. The concentration of the aliphatic polyester is preferably not less than 1 wt % because such a low concentration will make it difficult to form a fiber structure. It is also preferably not greater than 30 wt % because the fiber size of the resulting fiber structure will be too large. The concentration of the aliphatic polyester is more preferably 2-20 wt %.

The volatile solvent used to form the solution of the invention is a substance which dissolves the aliphatic polyester, has a boiling point of no greater than 200° C. at ordinary pressure, and is liquid at 27° C.

As examples of specific volatile solvents there may be mentioned methylene chloride, chloroform, acetone, methanol, ethanol, propanol, isopropanol, toluene, tetrahydrofuran, 1,1,1,3,3,3-hexafluoroisopropanol, water, 1,4-dioxane, carbon tetrachloride, cyclohexane, cyclohexanone, N,N-dimethylformamide and acetonitrile. Particularly preferred among these are methylene chloride, chloroform and acetone, from the standpoint of solubility of the aliphatic polyester.

These solvents may be used alone or in combinations of two or more. According to the invention, other solvents may also be used therewith so long as the object of the invention is not prevented.

Figure 2:
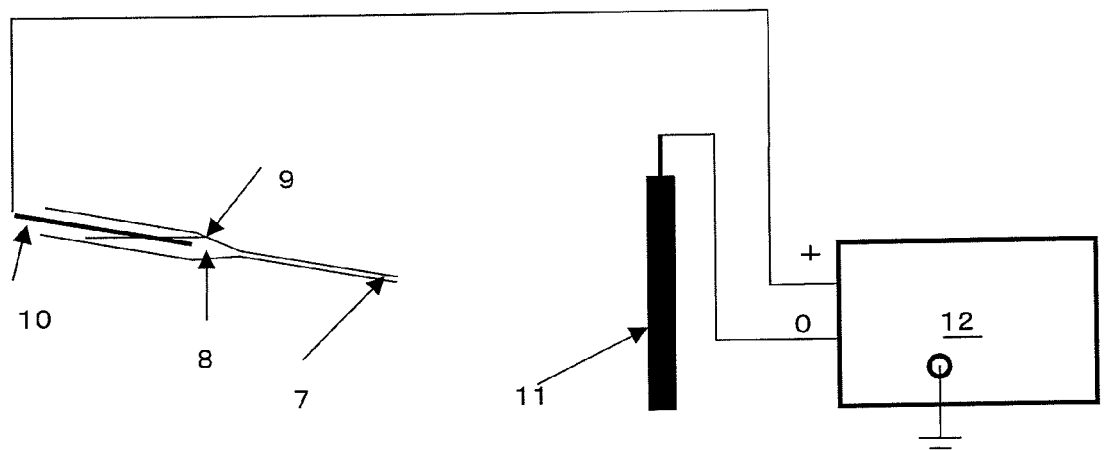
FIG. 2 is an example of an apparatus used in an electrostatic spinning method wherein fine droplets of the spinning solution are introduced into an electrostatic field, as a production method of the invention.
Figure 3:
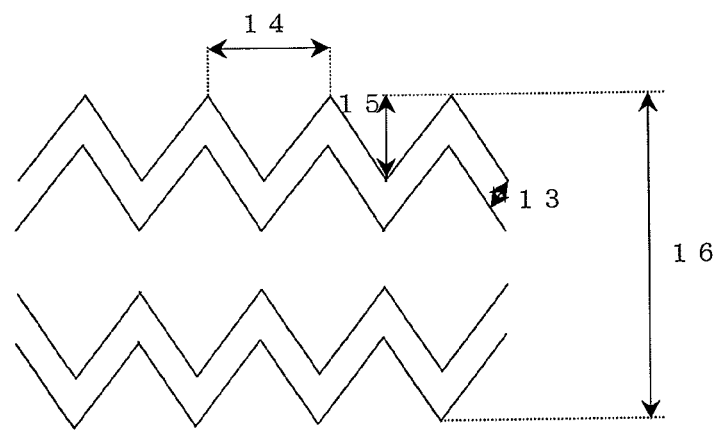
FIG. 3 is a cross-sectional view of a cylindrical body according to the invention.

The following is a brief description of the reference numerals used in FIGS. 1 to 3.

| | |
|---|---|
| 1 | Solution ejection nozzle |
| 2 | Solution |
| 3 | Solution holding tank |
| 4 | Electrode |
| 5 | Fiber substance collecting electrode |
| 6 | High-voltage generator |
| 7 | Solution ejection nozzle |
| 8 | Solution |
| 9 | Solution holding tank |
| 10 | Electrode |
| 11 | Fiber substance collecting electrode |
| 12 | High-voltage generator |
| 13 | Thickness |
| 14 | Bellows-shaped section spacing |
| 15 | Depth |
| 16 | Diameter |

Any desired method may be used for discharge of the solution into the electrostatic field. An example will now be explained with reference to FIG. 1. The solution 2 is supplied to a nozzle and situated at a suitable position in the electrostatic field, and the solution is drawn from the nozzle by the electric field to form a filament. Any suitable apparatus may be used for this purpose, and for example, an injection needle-type solution ejection nozzle 1 having a voltage applied by appropriate means such as a high-voltage generator 6, may be set at the tip end of the cylindrical solution holding tank 3 of an injector, and the solution directed to the tip. The tip of the ejection nozzle 1 may be placed at an appropriate distance from a grounded fiber substance collecting electrode 5, so that a fiber substance is formed between the tip and the fiber substance collecting electrode 5 when the solution 2 leaves the tip of the ejection nozzle 1.

It will be readily apparent to a person skilled in the art that fine droplets of the solution may also be introduced into the electrostatic field by a self-evident method. An example thereof will now be explained with reference to FIG. 2. The sole condition for this method is that the droplets must be held at a distance from the fiber substance collecting electrode 11 which allows fiber formation to occur in the electrostatic field. For example, an electrode 10 directly opposing the fiber substance collecting electrode 11 may be inserted directly into the solution 8 in the solution holding tank 9 comprising a nozzle 7.

A plurality of nozzles may be used to increase the fiber substance production speed when the solution is supplied from the nozzle into the electrostatic field. The distance between the electrodes will depend on the charge, the nozzle dimensions, the spinning solution flow rate and the spinning solution concentration, but a distance of 5-20 cm is appropriate for about 10 kV. The electrostatic potential applied will generally be 3-100 kV, preferably 5-50 kV and more preferably 5-30 kV. The desired potential may be created by any suitable method.

The explanation given above is for an electrode also serving as the collector, but a member serving as the collector may be situated between the electrodes as a collector separate from the electrodes. Also, the shape of the collector may be selected so as to yield a sheet or tube. In addition, for example, a belt-shaped material may be set between the electrodes as a collector to allow continuous production.

According to the invention, the solvent evaporates in response to the conditions while the solution is being drawn to the collector, thus forming a fiber substance. At ordinary room temperature, the solvent will completely evaporate during the period until the substance is collected on the collector, but the drawing may be carried out under reduced pressure conditions if evaporation of the solvent is inadequate. Also the temperature for drawing will depend on the evaporation behavior of the solvent and the viscosity of the spinning solution, but will ordinarily be 0-50° C. Accumulation of the fiber substance on the collector produces a fiber structure.

The method used for production of a cylindrical body composed of the fiber structure of the invention is not particularly restricted, but using a mandrel which has not been mirror surface-finished as the collector for electrostatic spinning is preferred since it will allow more convenient production of the cylindrical body. Specifically, by forming the fiber structure to a prescribed basis weight on the mandrel by electrostatic spinning and then removing the fiber structure from the mandrel while maintaining a suitable degree of friction, it is possible to conveniently obtain a cylindrical body having a bellows-shaped section.

The surface roughness of the mandrel is preferably 0.2-S or greater, and more preferably 1.5-400-S.

When the fiber structure is removed from the mandrel having a suitable surface roughness as described above, it is preferred to apply stress only to one end of the fiber structure. The end of the fiber structure may be secured and the mandrel pulled out in the direction toward the secured end to apply stress only to that end.

Also, when the fiber structure is formed on the mandrel by electrostatic spinning, it is preferred to rotate the mandrel in the circumferential direction to form a more uniform cylindrical body.

The cylindrical body obtained according to the invention may be used alone, but it may also be used in combination with other members for reasons of handleability or other required performance. For example, by combining the cylindrical body with an elastic body made of collagen or the like, it is possible to construct a member exhibiting optimal elasticity and strength.

The source of the collagen used for the invention is not particularly restricted, and it may be derived from any organism such as a mammal, bird, fish or the like. Collagen produced by cells such as bacteria, mold or yeast may also be used. Organism-derived collagen is preferably mammalian collagen, while collagen from cells such as bacteria, mold or yeast may be a recombinant form obtained by gene manipulation. There is also no particular restriction on the chemical structure of the collagen, which may be acid-solubilized collagen, neutral salt-solubilized collagen, enzyme-solubilized collagen, alkali-solubilized collagen or the like. Any desired amino acid sequences, such as telopeptides, of the collagen, as well as saccharides bonded to the collagen, may be removed depending on the purpose of use, and atelocollagen is preferred.

When the collagen is isolated from an organism, there are no particular restrictions on the method of isolation. The soluble components extracted with aqueous acidic solutions or aqueous alkaline solutions are preferred for use. The collagen obtained by extraction may be used directly in the form of an aqueous acidic solution or aqueous alkaline solution, but it is preferred to remove the excess low molecular ions by dialysis or ion exchange.

The means for forming the composite of the fiber structure and collagen according to the invention is preferably the following method. Preferably, a solution of the collagen dissolved and/or dispersed in an appropriate solvent is impregnated into the fiber structure and then fixed by at least one method such as gelling, crosslinking or drying, to form a collagen network.

In this case, if the collagen dissolves in the solvent it may be utilized as a collagen solution, and if it does not dissolve in the solvent it may be utilized as a dispersion. Also, when a portion of the collagen dissolves or swells but does not completely dissolve, both the solution and dispersion may be utilized for the invention.

Any solvent may be selected, including water, amide-based solvents such as dimethylacetamide and sulfone-based solvents such as dimethylsulfoxide, but water is preferably used. In addition, an inorganic salt such as calcium chloride or lithium chloride, a polyhydric alcohol such as glycerin or polyethylene glycol or a surfactant such as glycerin monostearate may be mixed into the solvent if necessary.

There are no particular restrictions on the method of impregnating the collagen into the fiber structure, and it may be carried out at ordinary pressure, under reduced pressure or under pressurization. A die may also be used to form an appropriate shape for the cylindrical body.

Gelling is a procedure whereby the collagen is gelled by heating under neutral conditions, and there are no particular restrictions on the reagent used for pH adjustment. Crosslinking involves reacting the collagen with a compound having two or more functional groups which can react with collagen, and it is preferred to use a compound with a carbodiimide group or a compound with an active ester group.

The collagen concentration of the collagen solution, dispersion or semi-solution is preferably at least 0.1% and no greater than 10%. It is more preferably in the range of at least 0.2% and no greater than 8%.

The cylindrical body disclosed by the present invention may be lyophilized if necessary. The conditions for lyophilization are not particularly restricted, but preferably the lyophilization temperature is no higher than −5° C., and the vacuum degree during lyophilization is no greater than 100 MPa.

The collagen impregnated into the fiber structure may be a porous form depending on the purpose. The method of forming pores is not particularly restricted, and sponge-like pores produced by lyophilization are also desirable for use. The collagen may also contain particles which are soluble in organic solvents, and a method may be employed for their subsequent extraction with an organic solvent. The fiber surfaces may also be coated with collagen for maximum utilization of the spaces of the fiber structure.

The composite obtained according to the invention may be used alone, but it may also be used in combination with other members for reasons of handleability or other required performance. For example, additives such as glycerin or polyethylene glycol may be included in order to increase the flexibility of the composite as a whole, or proteins such as growth factors and cytokines may also be added.

EXAMPLES

The present invention will now be explained in greater detail through the following examples, with the understanding that the invention is in no way limited to these examples.

The polylactic acid (Lacty9031) used in these examples is a product of Shimadzu Laboratories, and the methylene chloride (high grade) used is a product of Wako Pure Chemical Industries Co., Ltd.

Example 1

A dope was prepared by mixing 1 g of polylactic acid and 8 g of methylene chloride at room temperature (25° C.). An apparatus such as shown in FIG. 2 was used for 5 minutes of discharge of the solution to a fiber substance collecting electrode 5 (2 mm diameter, 200 mm length, 70-S surface roughness), causing rotation at 60 rpm. During this time, the collecting electrode 5 was rotated 150 rpm in the circumferential direction. The inner diameter of the ejection nozzle 1 was 0.8 mm, the voltage was 12 kV, and the distance from the ejection nozzle 1 to the fiber substance collecting electrode 5 was 10 cm. The end of the fiber structure collected at the fiber substance collecting electrode 5 was held fixed against a finger while the fiber substance collecting electrode 5 was pulled out toward the end fixed against the finger, to obtain a polylactic acid tube. The obtained polylactic acid tube had a diameter of 2 mm, a length of 20 mm, a basis weight of 20 g/m$^2$, a bellows-shaped section spacing of 0.5 mm and a bellows-shaped section depth of 0.1 mm. The Young's modulus and yield elongation of the obtained molded article were measured using a Tensilon device (INSTRON) with reference to DIN53507, 53504. The results are shown in Table 1.

TABLE 1

Physical property values for materials

|  | Material | Basis weight (g/m²) | Spacing of bellows-shaped section (mm) | Young's modulus (MPa) | Yield elongation (%) |
|---|---|---|---|---|---|
| Example 1 | Polylactic acid | 20 | 0.5 | 20 | 50 |
| Example 2 | Polylactic acid | 40 | 0.5 | 35 | 30 |
| Comp. Ex. 1 | Polylactic acid | 100 | 0.5 | 170 | 5 |
| Comp. Ex. 2 | Polylactic acid | 20 | 3.0 | 100 | 10 |

Example 2

The same treatment was carried out as in Example 1, except that the basis weight was 40 g/m².

Example 3

A 2 mm-diameter rod was reinserted into the polylactic acid tube obtained in Example 1, and this was fixed at the center of a 3 mm diameter tube. A 1.5 unit volume of a buffer solution containing 260 mM sodium bicarbonate, 200 mM HEPES and 50 mM sodium hydroxide was mixed with a 10 unit volume of 0.3% aqueous (type II) collagen solution by Koken Co., Ltd., while cooling on ice, and the mixture was placed in the holding tube in which the polylactic acid tube was fixed. A procedure in which the external atmosphere pressure was reduced and restored to ordinary pressure was repeated three times, and then the tube was kept at 37° C. for gelling. After gelling, the 2 mm diameter rod was pulled out and lyophilization was carried out to obtain a collagen cylindrical body.

The yield elongation of the obtained molded article was measured using a Tensilon device (INSTRON) with reference to DIN53507, 53504, giving a yield elongation value of 38%.

Comparative Example 1

The same treatment was carried out as in Example 1, except that the basis weight was 100 g/m².

Comparative Example 2

The same procedure was carried out as in Example 1, except that a different fiber substance collecting electrode 5 (2 mm diameter, 200 mm length, mirror surface finish (surface roughness: =0.1-S)) was used. The same treatment was carried out as in Example 1, except that the obtained polylactic acid tube had a basis weight of 20 g/m² and a bellows-shaped section spacing of 3.0 mm.

Comparative Example 3

A dope was prepared by mixing 0.5 g of polylactic acid and 10 g of methylene chloride at room temperature. The dope was packed into an HG-S Spray Gun (product of Tamiya Inc.) having a nozzle aperture of 0.2 mm, and an air pressure of 0.08 MPa was used for blowing into a rotating 2 mmf diameter rod. The fiber structure formed on the rod surface was removed off, producing a fiber structure with no bellows-shaped section, and having a basis weight of 50 g/m² and a thickness of 0.3 mm. This was used to form a composite with collagen in the same manner as Example 3, and the yield elongation was measured to be 8%.

Industrial Applicability

According to the invention it is possible to obtain a collagen/fiber composite structure exhibiting excellent stretchability. The collagen composite may be utilized as a vessel-substituting material such as an artificial vessel, or for regeneration of nerves or urinary ducts. It may also be employed as a cell culturing support in a test tube, or as an experimental material for cell evaluation.

What is claimed is:

1. A method for the production of a cylindrical body composed of a fiber structure with a basis weight of 1-50 g/m², wherein the cylindrical body has a bellows-shaped section, wherein the spacing of the bellows-shaped section is no greater than 2 mm and the depth of the bellows-shaped section ranges from 0.01-0.1 mm, the method comprising:
   1) producing a solution of an aliphatic polyester in a volatile solvent, 2) spinning said solution by an electrostatic spinning method to form a fibrous structure on a mandrel having a surface roughness ranging from 0.2-S to 400-S, and 3) forming the bellows-shaped section by first securing one end of the formed fibrous structure against the mandrel and then pulling said mandrel out of the fibrous structure in the direction toward the secured end.

2. A method for production of a composite composed of a cylindrical body and collagen, wherein a composite is formed of a cylindrical body produced by a method according to claim 1, and collagen.

3. A method for production of a composite composed of a cylindrical body and collagen, wherein a cylindrical body produced by a method according to claim 1 is impregnated with a solution comprising collagen dissolved and/or dispersed in a solvent, and then at least one method is employed to fix the collagen by gelling, crosslinking or drying.

* * * * *